(12) United States Patent
Boudreaux et al.

(10) Patent No.: US 10,307,204 B2
(45) Date of Patent: Jun. 4, 2019

(54) INTEGRATED BAILOUT FOR MOTORIZED RF DEVICE

(71) Applicant: Ethicon Endo-Surgery, LLC, Guaynabo, PR (US)

(72) Inventors: Chad P. Boudreaux, Cincinnati, OH (US); Catherine A. Corbett, Cincinnati, OH (US); Rudolph H. Nobis, Mason, OH (US); Mark D. Overmyer, Cincinnati, OH (US); Aaron C. Voegele, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 593 days.

(21) Appl. No.: 14/940,436

(22) Filed: Nov. 13, 2015

(65) Prior Publication Data

US 2017/0135717 A1 May 18, 2017

(51) Int. Cl.
  *A61B 17/32* (2006.01)
  *A61B 18/14* (2006.01)
  *A61B 17/295* (2006.01)
  *A61B 17/00* (2006.01)

(52) U.S. Cl.
  CPC .. *A61B 18/1445* (2013.01); *A61B 17/320092* (2013.01); *A61B 2017/00398* (2013.01); *A61B 2017/320093* (2017.08); *A61B 2017/320094* (2017.08); *A61B 2018/1455* (2013.01)

(58) Field of Classification Search
  CPC ......... A61B 2017/00353; A61B 2017/320094; A61B 2017/320093; A61B 2017/00398; A61B 2017/00734; A61B 2090/08021; A61B 18/1445; A61B 2018/1455; A61B 2018/00607; A61B 17/285; A61B 17/29; A61B 17/295
  See application file for complete search history.

(56) References Cited

U.S. PATENT DOCUMENTS

| 2009/0202387 A1 | 8/2009 | Dlugos, Jr. et al. |
| 2010/0089970 A1 * | 4/2010 | Smith ............... A61B 17/07207 227/175.1 |

* cited by examiner

*Primary Examiner* — Eric J Rosen
*Assistant Examiner* — Mikail A Mannan
(74) *Attorney, Agent, or Firm* — Mintz Levin Cohn Ferris Glovsky and Popeo, P.C.

(57) ABSTRACT

Methods and devices are provided for retracting a cutting assembly in the event of a failure on a motorized electrosurgical device. For example, a surgical device is provided that includes a handle portion with an elongate shaft that has first and second jaws configured to engage tissue. The device also includes a cutting assembly configured to cut tissue engaged between the first and second jaws and a drive shaft that moves the cutting assembly. A gear box is provided in the device that is coupled to the drive shaft, and a motor is coupled to the gear box for driving the gear box. The device has a normal mode in which power can be provided to the motor to drive the gear box, and the device has a bailout mode in which the motor and gear box can be manually rotated as a unit.

12 Claims, 5 Drawing Sheets

INTEGRATED BAILOUT FOR MOTORIZED RF DEVICE

FIELD

Methods and devices are provided for retracting a cutting assembly in the event of a failure on a motorized electrosurgical device.

BACKGROUND

Endoscopic surgical instruments are often preferred over traditional open surgical devices since a smaller incision associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, stapler, clip applier, access device, drug/gene therapy delivery device, and energy device using ultrasound, RF, laser, etc.).

Endoscopic devices are passed through an access port, such as a trocar, to allow the distal end effector to engage tissue within a body cavity of a patient. With powered devices, any problems that occur may prevent removal of the device through the access port. For example, in the event the end effector becomes jammed during a firing stroke or the device otherwise fails, the end effector cannot be removed because tissue is engaged between the jaws. The surgeon may be forced to open up the patient and cut the instrument out of the patient, potentially causing serious harm to the patient.

Accordingly, there remains a need for methods and devices for retracting a cutting assembly in the event of a failure on a motorized electrosurgical device.

SUMMARY

Various methods and devices are provided for retracting a cutting assembly in the event of a failure on a motorized electrosurgical device.

In one aspect, a surgical device is provided that includes a handle portion, a cutting assembly, a drive shaft, a gear box, and a motor. The handle portion has an elongate shaft that extends distally therefrom with first and second jaws at a distal end thereof that are configured to engage tissue therebetween. The cutting assembly is configured to move relative to the first and second jaws so as to cut tissue engaged between the first and second jaws, and a drive shaft extends from the handle through the elongate shaft and is coupled to the cutting assembly for moving the cutting assembly relative to the first and second jaws. The gear box is coupled to the drive shaft and moves the drive shaft proximally and distally, and the motor is coupled to the gear box to drive the gear box. The device has a normal mode in which power can be provided to the motor to drive the gear box and cause movement of the drive shaft, and the device also has a bailout mode in which the motor and gear box can be manually rotated as a unit to cause movement of the drive shaft.

The surgical device can vary in a number of ways. For example, power can be disconnected from the motor in the bailout mode. In another example, the handle portion can include a shroud around the motor and gear box that is configured to separate from the handle portion in the bailout mode. As another example, the shroud can be configured to reconnect to the handle portion to transition back to the normal mode. In yet another example, a cap on the end of the handle portion can be movable from a first position in which the cap is mated to the handle portion to a second position in which the cap is partially separated from the handle portion and is freely rotatable relative to the handle portion, rotation of the cap causing rotation of the motor and the gear box. In another example, power can be disconnected from the motor when the cap is moved to the second position. In still another example, a lever on the end of the handle portion can be movable from a first position in which the lever is fixed relative to the handle portion to a second position in which the lever is rotatable relative to the handle portion, rotation of the lever causing rotation of the motor and the gear box. In another example, movement of the lever to the second position can cause power to be disconnected from the motor.

In yet another example, a cap on the end of the handle portion can be removable from the handle portion, and a knob can be coupled to an end of the motor and can be accessible upon removal of the cap. The knob can also be configured to cause rotation of the motor and the gear box upon rotation of the knob. In another example, movement of the lever to the second position can cause power to be disconnected from the motor.

In another aspect, a surgical device is provided that includes a handle, a cutting assembly, a motorized gear assembly, and a bailout lever. The handle has an elongate shaft that extends distally therefrom with first and second jaws at a distal end thereof that engage tissue therebetween. The cutting assembly is movable relative to the first and second jaws to cut tissue engaged between the first and second jaws, and the motorized gear assembly is coupled to the cutting assembly for moving the cutting assembly relative to the first and second jaws. The bailout lever is positioned on the handle and is movable from a first disengaged position, in which the bailout lever is disengaged with the motorized gear assembly, to a second engaged position, in which the bailout lever is engaged with the motorized gear assembly and is effective to manually drive the motorized gear assembly.

The surgical device can vary in a number of ways. For example, movement of the bailout lever to the second engaged position can cause power to be disconnected from the motorized gear assembly. In another example, movement of the bailout lever from the second engaged position back to the first disengaged position can cause power to be reconnected to the motorized gear assembly. As another example, movement of the bailout lever to the second engaged position can cause the bailout lever to partially disengage from the handle. As yet another example, the bailout lever can be configured to rotate the motorized gear assembly in the second engaged position.

In another aspect, a method for cutting tissue is provided that includes engaging tissue between first and second jaws on a surgical device. The method can also include actuating the surgical device to cause power to be delivered to a motor such that the motor drives a gear box which drives a drive shaft to move a cutting assembly through the first and second jaws to at least partially cut the tissue engaged between the first and second jaws. The method can further include manually rotating the motor and gear box to cause movement of the drive shaft and the cutting assembly.

The method can vary in any number of ways. For example, manually rotating the motor and gear box can include disconnecting power from the motor and gear box. As a further example, the method can include, after manually rotating the motor and gear box, reconnecting power to the motor and gear box. As another example, manually rotating the motor and gear box can include rotating a shroud coupled to the motor and gear box where the shroud is at least partially separatable from the surgical device. The method can also include, after manually rotating the motor and gear box, reconnecting the shroud to the surgical device. As still another example, manually rotating the motor and gear box can include removing a cap from around the motor. As yet another example, manually rotating the motor and gear box can include rotating a bailout lever on the surgical device that engages with the motor and gear box. As another example, rotating a bailout lever on the surgical device that engages with the motor and gear box can include disconnecting power to the motor.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for retracting a cutting assembly in the event of a failure on a motorized electrosurgical device. In particular, methods and devices are provided for disconnecting power between a processor and a motor and for rotating a motor and gear box on a motorized electrosurgical device.

Figure 1:
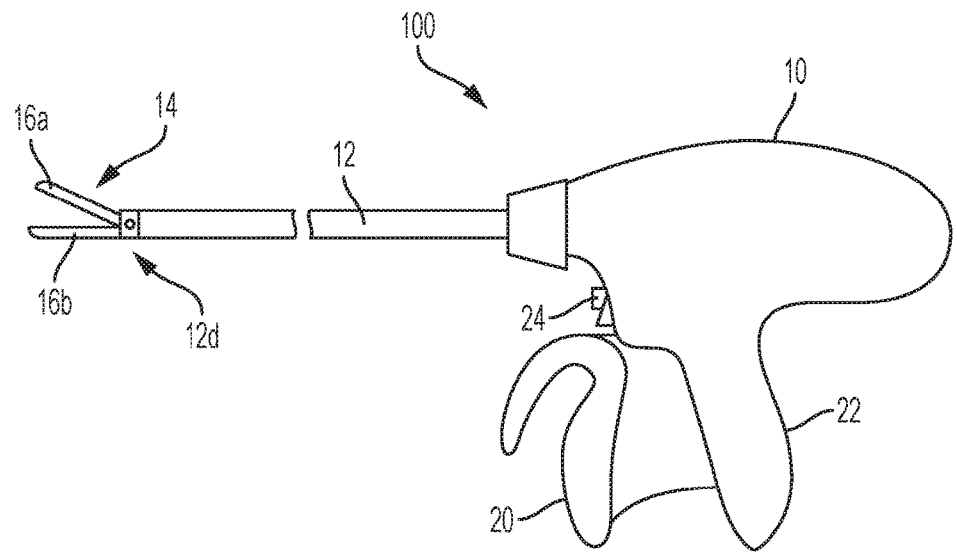
FIG. 1 is a side view illustration of one embodiment of a powered surgical device.

FIG. 1 illustrates one embodiment of a surgical device configured to grasp and cut tissue. As shown, the illustrated surgical device 100 generally includes a proximal handle portion 10, a shaft portion 12, and an end effector 14 for grasping tissue. The proximal handle portion 10 can be any type of pistol-grip, scissor grip, pencil-grip, or other type of handle known in the art that is configured to carry various actuators, such as actuator levers, knobs, triggers, or sliders, for actuating various functions such as rotating, articulating, approximating, and/or firing the end effector 14. In the illustrated embodiment, the proximal handle portion 10 includes a stationary grip 22 and a closure grip 20 that is movable toward and away from the stationary grip 22 to open and close jaws of the end effector 14. The shaft portion 12 extends distally from the proximal handle portion and has a lumen (not shown) extending therethrough for carrying mechanisms for actuating the end effector 14.

The end effector can have a variety of sizes, shapes, and configurations. As shown in FIG. 1, the end effector 14 includes a first upper jaw 16a and a second lower jaw 16b disposed at a distal end 12d of the shaft portion 12. The jaws 16a, 16b are moveable between an open position in which the jaws 16a, 16b are spaced a distance apart, and a closed position in which the jaws 16a, 16b are moved toward one another and are substantially opposed. When the jaws 16a, 16b are in the closed position, a longitudinal axis of the upper jaw 16a can be substantially parallel to a longitudinal axis of the lower jaw 16b and the jaws 16a, 16b can be in direct contact for engaging tissue therebetween. In the illustrated embodiment, the upper jaw 16a pivots relative to the shaft portion 12 and relative to the lower jaw 16b while the lower jaw 16b remains stationary. While the illustrated jaws 16a, 16b have a substantially elongate and straight shape, a person skilled in the art will appreciate that one or both of the jaws 16a, 16b can be in various directions. The jaws 16a, 16b can have any suitable axial length for engaging tissue, and the length can be selected based on the targeted anatomical structure for transection and/or sealing.

As indicated above, the surgical device 100 can have a closure actuator that can be configured to open and close the jaws 16a, 16b of the end effector 14. Manipulation of the closure actuator can pivot or otherwise move the jaws relative to one another such that the jaws can engage tissue, move anatomical structures, or perform other surgical functions. The closure actuator can have various sizes, shapes, and configurations, but in the illustrated embodiment the closure actuator includes the closure grip 20 and the stationary grip 22. The closure grip 20 can be moveable toward and away from stationary grip 22, such as via pivoting. In particular, the closure grip 20 can have a first position in which it is angularly offset and spaced apart from the stationary grip 22 and the jaws 16a, 16b of the end effector 14 are open. The closure grip 20 can have a second position where it is positioned adjacent to, or substantially in contact with, the stationary grip 22 and the jaws 16a, 16b of the end effector 14 can engage tissue and apply a force to tissue disposed therebetween. The closure grip 20 can be biased to the first open position with the jaws 16a, 16b of the end effector 14 being open, as shown in FIG. 1. The closure grip 20 can move the jaws 16a, 16b between the open and closed positions using manual or powered components. For example, in manually actuated embodiments, the closure grip 20 can be coupled to gears that interact with a rack disposed within the handle. Manual movement of the closure grip 20 toward the stationary grip 22 can move the rack either proximally or distally relative to the end effector 14 to either pull or push the jaws 16a, 16b closed. In other embodiments, the drive shaft can include or be coupled to a drive screw which can be moved proximally by a drive nut that is rotated by a series of gears. In powered embodiments, a motor can be disposed in the proximal handle portion 10 and manual movement of the closure grip 20 can cause a control signal to be sent to the motor, which can interact with various gears or other components to cause the jaws 16a, 16b to close. The closure grip 20 can interact with one or more locking features (not shown) configured to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting.

In certain embodiments the surgical device can also have a second actuator, such as actuator 24, that can be separate from the closure actuator 20. The second actuator can be configured to advance a cutting assembly, apply energy to tissue, or both, and is referred to herein as a "firing actuator." The firing actuator 24 can have various sizes, shapes, and configurations, but in the illustrated embodiment it is in the form of a button or trigger that can be depressed by a user. In another embodiment, the firing actuator 24 can be in the form of a switch, lever, etc., that can be slid, pivoted, or otherwise moved by a user. Depressing or pivoting the actuator can activate various elements in the device, and can cause a cutting assembly to advance through the end effector and/or cause energy to be delivered to the jaws. For example, depressing or pivoting the firing actuator can cause a cutting assembly to advance distally and/or retract proximally relative to the jaws 16a, 16b. More specifically, the firing actuator can be in electrical communication with a motor disposed in the proximal handle portion 10. The motor can be operatively coupled to the cutting assembly using known components, such as one or more gears and a rack or drive screw.

Figure 2:
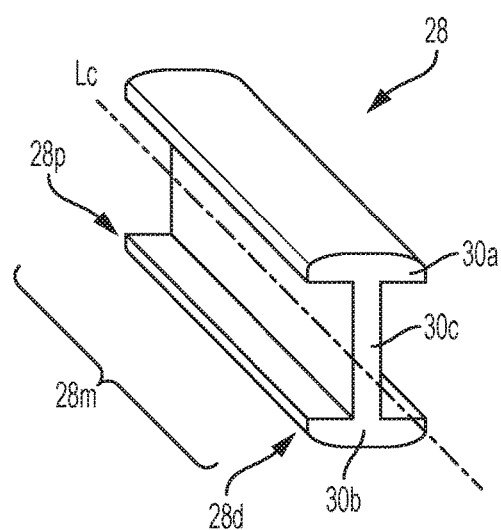
FIG. 2 is a perspective view illustration of a compression member of the powered surgical device of FIG. 1.

The cutting assembly can be configured to transect tissue captured between the jaws, and it can be sized and shaped to transect or cut various thicknesses and types of tissue. In one exemplary embodiment, as shown in FIG. 2, the cutting assembly can include an I-beam compression member 28 that travels through slots formed in each jaw to pull the jaws into a parallel orientation and to compress tissue therebetween. The compression member 28 can include a cutting element (not shown) positioned at the distal end 28d thereof and formed on a connecting portion 30c of the compression member 28. In some embodiments, the cutting element can be integrally formed with the distal end 28d of the compression member 28. The cutting element can have a sharp or serrated edge configured to transect the tissue. In some embodiments, the cutting element can be recessed relative to distal ends of upper and lower flanges 30a, 30b of the I-beam compression member 28 so that compression occurs prior to transecting or cutting of the tissue. In another embodiment, the cutting element can include a shaft having a knife blade that is not attached to a compression member such that the cutting assembly can advance and retract relative to the jaws without applying compression to the tissue.

Figure 3:
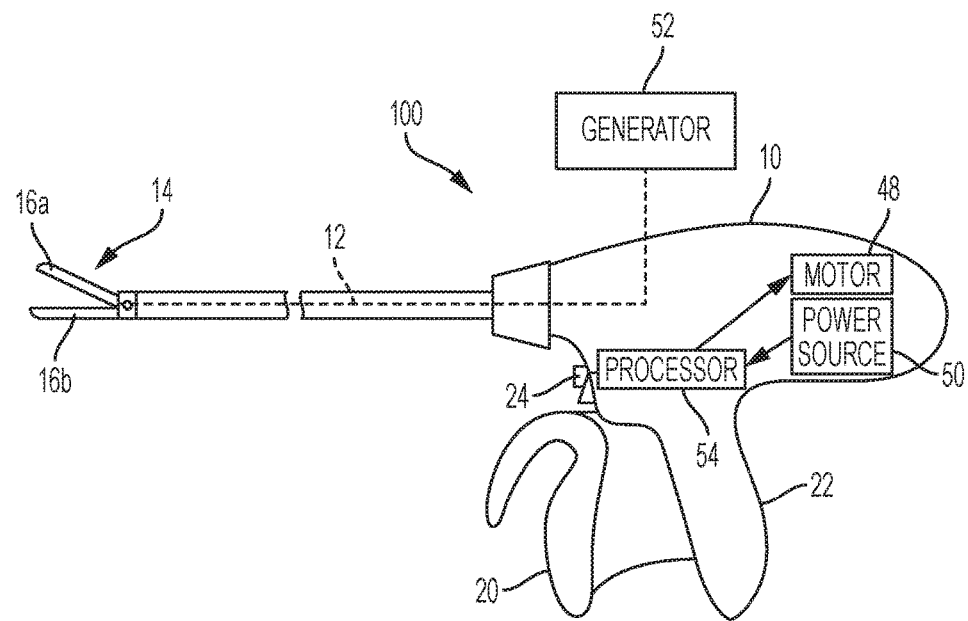
FIG. 3 is another side view illustration of the powered surgical device of FIG. 1, schematically illustrating various components in the handle of the device.

As shown in FIG. 3, the handle portion 10 of the surgical device 100 can include components for operating the device, such as a motor 48, a power source 50, a generator 52, and a processor 54, as well as various sensors (not shown). The device 100 can also include various components for delivering energy, such as radiofrequency or ultrasound energy, to tissue, and these components can be disposed at various locations in the device 100, such as in the proximal handle portion 10 and/or in the jaws 16a, 16b. The firing actuator 24 can be coupled to the processor 54, and the processor 54 can be coupled to the motor 58, the power source 50, and/or the generator 52 (as well as any sensors provided). Firing the actuator 24 sends a signal to the processor 54, which can cause the power source 50 to provide power to the motor 48 through the processor 54. The motor 48 can drive the cutting assembly, and the processor 54 can control a speed and a direction of the motor, which in turn alters a speed and a direction of the cutting assembly.

The generator 52 can be a separate unit that is electrically connected to the surgical device 100 to decrease the size and weight of the surgical device 100, and it can be operatively coupled to an actuator on the surgical device so that the device is configured to apply energy to tissue engaged by the end effector when the actuator is activated. The generator can be operably coupled to the firing actuator 24 or the generator can be coupled to a second actuator. The generator can be any suitable generator known in the art, such as an RF generator or an ultrasound generator. A lumen (not shown) of the shaft portion 12 can carry electrical leads or wires that can deliver electrical energy to components of the end effector 14. The generator 52 can be coupled to the power source 50, such as a battery disposed in the proximal handle portion 10 or it can be coupled to an external power source, such as an electrical outlet.

Figure 4:
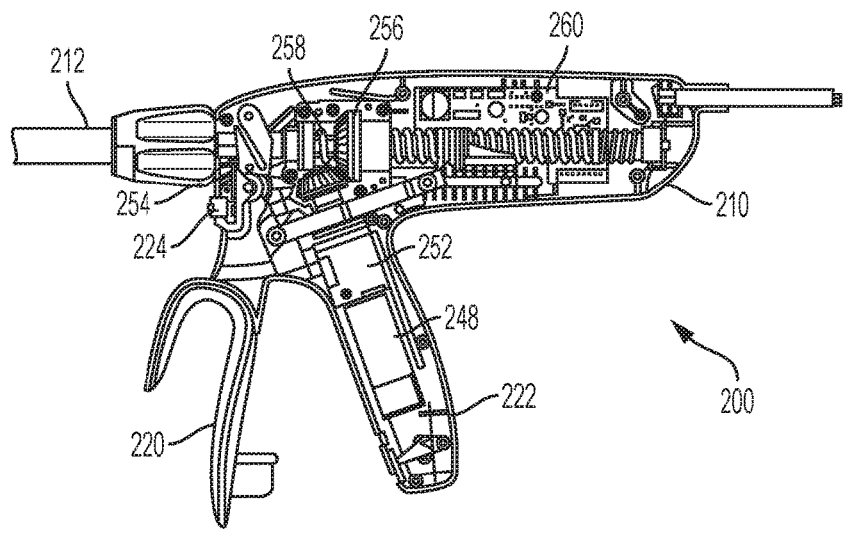
FIG. 4 is a side cutaway view of another embodiment of a powered surgical device.

FIG. 4 illustrates one exemplary configuration of a surgical device 200 having components for operating the device. The surgical device 200 can generally be configured and used similar to the surgical device 100 of FIGS. 1-3. As seen in FIG. 4, the surgical device 200 has a shaft portion 212, and a proximal handle portion 210 including a closure grip 220 and a stationary grip 222. The surgical device 200 has a firing actuator 224 that is configured to advance distally and/or retract proximally a cutting assembly through an end effector (not shown) positioned on a distal end of the shaft portion 212. The firing actuator 224 is a button that can be depressed by a user. The firing actuator 224 is coupled to and in communication with a processor 260, which can include a circuit board and/or a controller. The processor 260 can in turn be in communication with a motor 248, a power source such as a battery, and/or a generator. The motor 248 is disposed in the proximal handle portion 210, and it can be operatively coupled to a gear box 252, which is operably coupled to a motor bevel gear 254. The motor bevel gear 254 is operably coupled in turn to a drive bevel gear 256, which is operably coupled to a drive shaft 258. Activation of the firing actuator 224 can thus provide a signal to the processor 260. The processor 260 can cause power to be delivered from the power source to the motor 248, which rotates the gear box 252. The gear box 252 causes the motor bevel gear 254 to rotate, which engages with and rotates the drive bevel gear 256, which drives the drive shaft 258 distally or proximally. Upon rotation of the drive bevel gear 256, the drive shaft 258 can be driven distally or proximally through known means, such as a thread along the drive shaft 258. Distal movement of the drive shaft 258 advances the cutting assembly distally through an end effector. Proximal movement of the drive shaft 258 retracts the cutting assembly proximally from the end effector. A person skilled in the art will appreciate that the drive shaft can be advanced and retracted using a number of different techniques, such as a rack system, one or more linkages, a ball bearing and nut system, a bevel and spur gear system, etc.

As indicated above, the surgical device 200 has a generator (not shown) that is operatively coupled to an actuator on the surgical device 200 so that the device 200 is configured to apply energy to tissue engaged by the end effector when the actuator is activated. The generator can be operably coupled to the firing actuator 224 or the generator can be coupled to a second actuator. The generator can be any suitable generator known in the art, such as an RF generator or an ultrasound generator. A lumen (not shown) of the shaft portion 212 can carry electrical leads or wires that can deliver electrical energy to components of the end effector.

Under normal operation of a surgical device as described above, power can be supplied from a power source, e.g., the battery, through a processor to a motor, resulting in distal or proximal movement of a cutting assembly through an end effector positioned on a distal end of the surgical device. In certain instances, the surgical device may fail to successfully complete a cutting stroke, for example if the device jams during cutting because of thick tissue or if a power failure occurs. Removing the surgical device from a patient before retracting the cutting assembly may cause significant harm to the patient, though. If the surgical device malfunctions during a firing stroke, i.e., prior to full advancement and full retraction of the cutting assembly, a surgeon may be required to retract the cutting assembly from the jaws of the end effector. Accordingly, a bailout mechanism is provided that can allow retraction of the cutting assembly in the event of a malfunction.

In general, a surgical device can be provided with a handle and an elongate shaft extending distally therefrom. The elongate shaft can have an end effector at a distal end thereof, which can have first and second jaws. The jaws can be configured to engage tissue therebetween. A cutting assembly can be configured to move relative to the first and second jaws so as to cut tissue engaged between the first and second jaws. The cutting assembly can be driven distally and proximally relative to the first and second jaws by a drive shaft extending from the handle through the elongate shaft. A gear box can be coupled directly or indirectly to the drive shaft, and a motor can be coupled to the gear box. The motor can drive the gear box, which can cause proximal and distal movement of the drive shaft. A processor can be in communication with the motor, and the processor can be configured to control the motor. A power source, such as a battery, can provide power to the motor through the processor. An actuator can be part of the surgical device, and the actuator can be configured to receive an input from a user. Actuation of the actuator can cause power from the power source to be supplied to the motor through the processor to move the cutting assembly. The device can have a normal mode and a bailout mode. In the normal mode, power can be provided to the motor to drive the gear box, which in turn can cause movement of the drive shaft. In the bailout mode, the motor and gear box can be manually rotated together to cause movement of the drive shaft. In the bailout mode, communication between the processor and/or the power source and the motor can be prevented. Movement of the drive shaft can cause retraction of the cutting assembly. The first and second jaws can then open to release tissue engaged between, and a surgeon can subsequently withdraw the surgical device from a patient. The bailout mode may allow a surgeon to rapidly remove the surgical device during any emergency situation, for example if normal operation of the device malfunctions, while minimizing any harm to the patient. Manual bailout of the cutting assembly in the form of rotating the motor and the gear box may also be simpler and less prone to human error than other mechanisms, ensuring a safe retraction during a potentially high-stress situation in which the surgeon is attempting to monitor the patient and safely remove the device at the same time.

Figure 5:
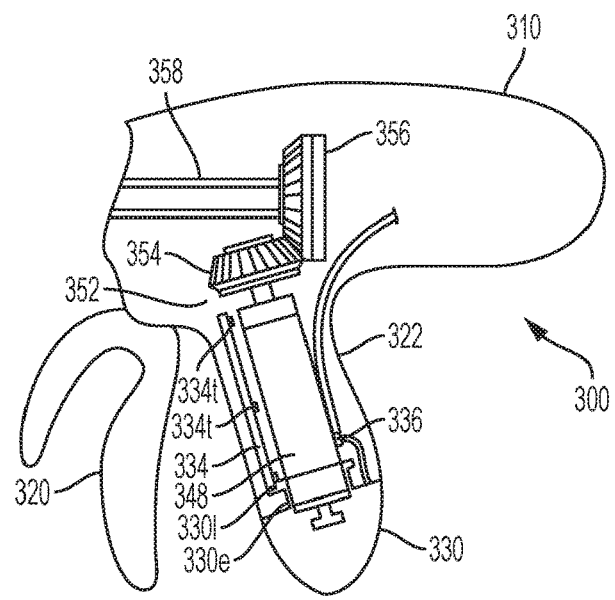
FIG. 5 is a partial side cutaway view of another embodiment of a powered surgical device with a bailout mechanism.
Figure 6:
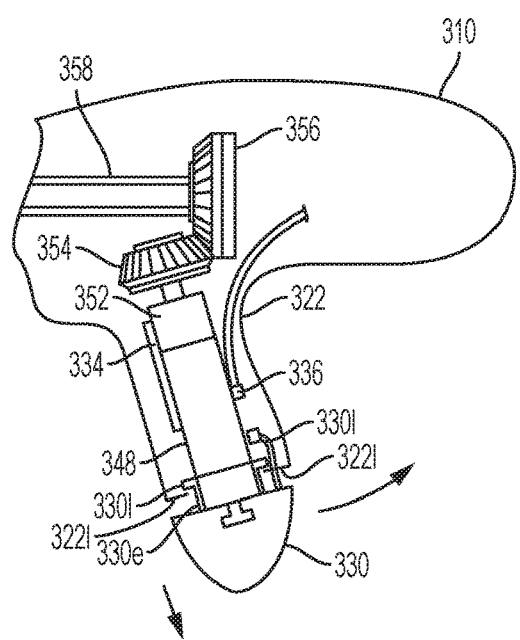
FIG. 6 is a partial side cutaway view of the powered surgical device of FIG. 5.

FIGS. 5-6 illustrate one embodiment of a surgical device 300 having a mechanical bailout. The surgical device 300 can generally be configured and used similar to the surgical devices 100, 200 of FIGS. 1-4. Surgical device 300 has a shaft portion (not shown), and a proximal handle portion 310 including a closure grip 320 and a stationary grip 322. The surgical device 300 has a firing actuator (not shown) that can be configured to advance distally and/or retract proximally a cutting assembly through an end effector (not shown) positioned on a distal end of the shaft portion. The closure grip 320 is effective to move jaws of the end effector between open and closed positions. The firing actuator is connected to and in communication with a processor (not shown) within the proximal handle portion 310. The processor is connected to and in communication with a motor 348 and a power source (not shown) such as a battery. The motor 348 is operably coupled to a gear box 352 and is disposed in the proximal handle portion 310. The motor 348 and the gear box 352 can be operatively coupled to a motor bevel gear 354 that is operably coupled (directly or indirectly) to a drive bevel gear 356, which in turn moves a drive shaft 358 proximally or distally.

In this embodiment, a cap 330 in a first position is coupled to a bottom of the stationary grip 322 and is coupled to the motor 348 on an end opposite to the gear box 352. The cap 330 has an extending portion 330e that extends around the motor 348 and a lip 3301 at a top edge of the extending portion 330e. A locking arm 334 can extend alongside the motor 348 and the gear box 352, however the locking arm 334 can be displaced from the motor 348 and the gear box 352 by the lip 3301 when the cap 330 is in the first position, allowing the motor 348 and the gear box 352 to rotate with respect to one another. In other words, the lip 3301 extends between the motor and the locking arm 334, holding the locking arm 334 a distance away from the motor 348. The cap 330 is not rotatable with respect to the stationary grip 322 in the first position.

The cap 330 is configured to move down and away from the motor 348 and the gear box 352 into a second position. The lip 3301 is configured to engage a corresponding lip 3221 on the stationary grip 322 upon moving the cap 330 to the second position. Engagement between lip 3301 and lip 3221 allows the cap 330 to be maintained on the stationary grip 322 but to be freely rotatable. As the cap 330 moves to the second position, the motor 348 and the gear box 352 are configured to lock and rotate together, for example by engagement of the locking arm 334. Upon movement of the cap 330 away from the motor 348, the lip 3301 is pulled away from the locking arm 334 thereby allowing the locking arm 334 to move against the motor 348 and the gear box 352 and to mechanically engage with each of the motor 348 and the gear box 352 through engagement tabs 334t on the locking arm 334. Because the locking arm 334 will mechanically engage with both the motor 348 and the gear box 352, the motor 348 and the gear box 352 are rotationally locked together. While engagement tabs 334t and the locking arm 334 are illustrated in this embodiment, any mechanism can be used to lock the motor and the gear box together to cause the motor and the gear box to rotate as a single unit, such as bars, cages, internal components between the motor and the gear box, etc.

Upon downward movement of the cap 330 to the second position, the cap 330 is rotatable with respect to the stationary grip 322 but not rotatable with respect to the motor 348 and the gear box 352. Movement of the cap 330 to the second position is also configured to break communication at a connection 336 between the motor 348 and the processor. Wires connecting the processor to the motor 348 run through the cap 330. The cap 330 mechanically ends communication between the processor and the motor 348 by physically breaking the connection of the wires between the motor 348 and the processor in the bailout mode, as seen in FIG. 6. Upon movement of the cap 330 away from the motor 348, the wires in the cap 330 are pulled away from the connection 336 and separate. Ending communication between the processor and the motor can be accomplished in a variety of different ways known in the art. For example, a sensor can be provided for detecting removal of the cap, and the sensor can send a signal to the processor that the bailout mode has been entered, at which point the processor can stop all signals to the motor until the normal mode is resumed. In such an embodiment, a connection between the motor and the processor would not run through the cap.

When the device 300 is in a normal mode, the cap 330 remains in place and communication between the processor and the motor 348 is maintained. Actuation of the firing actuator sends a signal to the processor. The processor provides power to the motor 348 from the power source. The motor 348 drives the gear box 352, which drives the motor bevel gear 354, in turn driving the drive bevel gear 356. The drive bevel gear 356 rotates, causing the drive shaft 358 to advance and retract. The drive shaft 358 fully advances distally and then fully retracts proximally the cutting assembly, representing one full cutting stroke.

In the event of a failure, the cap 330 can be moved downward away from the stationary grip 322, causing the device 300 to enter a bailout mode. Downward movement of the cap 330 separates the wires communicating between the motor 348 and the processor and thus ends communication between the processor and the motor 348, preventing accidental activation of the motor 348 in the bailout mode. As seen in FIG. 6, the cap 330 in the bailout mode is coupled to the stationary grip 322 to allow rotation of the cap 330 with respect to the stationary grip 322. The cap 330 remains coupled to the motor 348 in the bailout mode, and the motor 348 and the gear box 352 lock together due to the locking arm 334. The motor 348 and the gear box 352 also remain engaged with the motor bevel gear 354. Upon manual rotation of the cap 330 in the bailout mode, the motor 348 and the gear box 352 are both rotated with the cap 330, causing the motor 348 and the gear box 352 to rotate the motor bevel gear 354, which can ultimately rotate the drive bevel gear 356 to drive the drive shaft 358 and retract the cutting assembly.

The cap 330 is configured to allow rotation in either direction to allow both advancement and retraction of the cutting assembly. Other variations can allow rotation of the cap in only one direction to allow only retraction of the cutting assembly, for example by using a single-direction ratchet. The cutting assembly can be retracted as long as the cap is rotated. Other embodiments can include mechanisms to prevent over-retraction, such as a stopper positioned in the path of retraction in the proximal handle portion to contact the cutting assembly and prevent further retraction.

The cap 330 is configured to lock the motor 348 and the gear box 352 together during the bailout mode through engagement of the locking arm 334 such that the motor 348 and the gear box 352 rotate together. Other embodiments can allow the motor to be rotated with the cap while the motor rotates the gear box (as would occur in the normal mode) so that the motor and the gear box do not rotate together. Such an embodiment can be effective, for example, if the motor is connected to a gear box with a high mechanical advantage ratio.

The surgical device 300 can be reused and returned to the normal mode by moving the cap 330 back to its original position, which will reconnect the motor 348 and the processor and unlock the motor 348 and the gear box 352 from one another to allow individual rotation. Other variations can prevent the surgical device from being reused, effectively disabling the device, to prevent a malfunctioning surgical device from being used in other operations. For example, the cap can be irreplaceable, such as by adding a tab that would lock the cap in the bailout position, causing communication between the motor and the processor to be permanently disabled or through software upon detection of removal of the cap.

Figure 7:
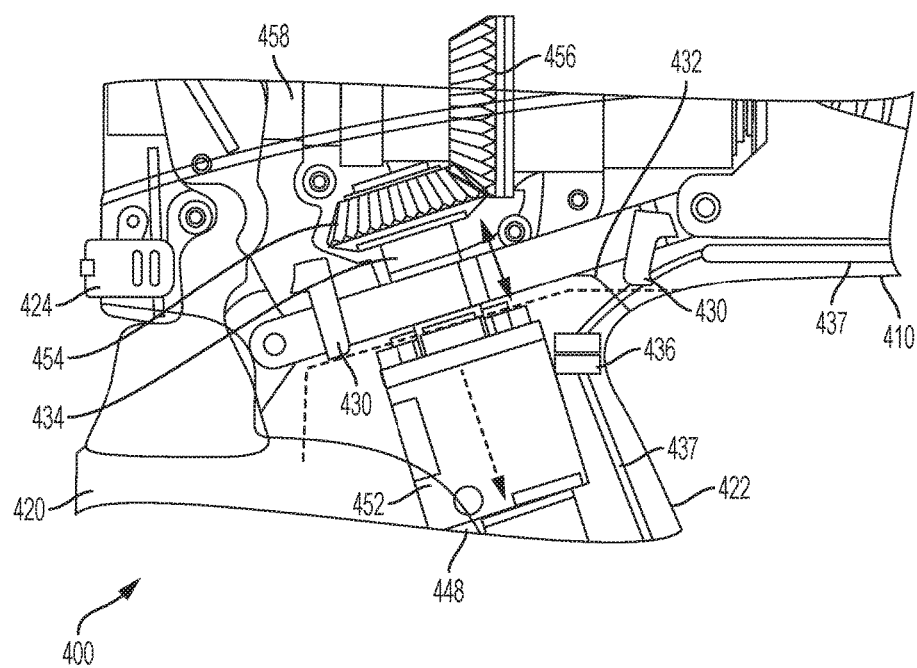
FIG. 7 is a partial side cutaway view of another embodiment of a powered surgical device with a bailout mechanism.

FIG. 7 illustrates another embodiment of a surgical device 400 having a mechanical bailout. The surgical device 400 can generally be configured and used similar to the surgical devices 100, 200 of FIGS. 1-4. Surgical device 400 has a shaft portion (not shown), and a proximal handle portion 410 including a closure grip 420 and a stationary grip 422. The surgical device 400 has a firing actuator 424 that can be configured to advance distally and/or retract proximally a cutting assembly through an end effector (not shown) positioned on a distal end of the shaft portion. The closure grip 420 is effective to move jaws of the end effector between open and closed positions. The firing actuator 424 is connected to and in communication with a processor (not shown) within the proximal handle portion 410. The processor is connected to and in communication with a motor 448 and a power source (not shown) such as a battery. The motor 448 is operably coupled to a gear box 452 and is disposed in the proximal handle portion 410. The motor 448 and the gear box 452 can be operatively coupled to a motor bevel gear 454 that is operably coupled (directly or indirectly) to a drive bevel gear 456, which in turn moves a drive shaft 458 proximally or distally.

In this embodiment, in a first position the stationary grip 422 is joined along the break line 432 to the proximal handle portion 410 and cannot be rotated with respect to the proximal handle portion 410. The stationary grip 422 acts as a shroud around the motor 448 and the gear box 452, and the stationary grip 422 is coupled to both the motor 448 and the gear box 452. An extendable shaft 434 couples the motor 448 and the gear box 452 to the motor bevel gear 454.

The stationary grip 422 is separable from the proximal handle portion along a break line 432 and thus can be moved down and away from the proximal handle portion 410 into a second position. The extendable shaft 434 telescopes in length upon downward motion of the motor 448 and the gear box 452 with the stationary grip 422 into the second position so that the motor 448 and the gear box 452 remain engaged with the motor bevel gear 454 through the telescoped extendable shaft 434. Locking arms 430 are coupled to the stationary grip 422 and are configured to engage the proximal handle portion 410 upon downward movement of the stationary grip 422. The locking arms 430 will thus maintain the stationary grip 422 at a desired distance from the proximal handle portion 410, similar to the lip 3301 and the lip 3221 of FIGS. 5-6. The locking arms 430 are also configured to lock into an extended position because tabs on an end of the locking arms 430 closest to the motor bevel gear 454 engage with the proximal handle portion 410. The locking arms 430 require depression before allowing any subsequent upward movement of the stationary grip 422. The stationary grip 422 is freely rotatable with respect to the proximal handle portion 410. The motor 448 and the gear box 452 are coupled within the stationary grip 422, resulting in the motor 448, the gear box 452, and the stationary grip 422 rotating as a single unit. Movement of the stationary grip 422 away from the proximal handle portion 410 is also configured to break communication at a connection 436 between the motor 448 and the processor because wires 437 creating the connection between the motor 448 and the processor run through the stationary grip 422. As the stationary grip 422 moves away from the proximal handle portion 410, wires 437 will also move away and break the connection at connection 436.

While the stationary grip 422 mechanically ends communication between the processor and the motor 448 by physically separating the wires 437 forming a connection between the motor 448 and the processor, ending communication between the processor and the motor can be accomplished in a variety of different ways known in the art. For example, a sensor in the stationary grip can sense downward movement of the stationary grip and send a signal to the processor that the bailout mode has been entered, at which point the processor can stop all signals to the motor until the normal mode is resumed. In such an embodiment, a connection between the motor and the processor would not be physically disconnected by downward movement of the stationary grip.

When the device 400 is in a normal mode, the stationary grip 422 remains in place and communication between the processor and the motor 448 is maintained. Actuation of the firing actuator 424 sends a signal to the processor. The processor provides power to the motor 448 from the power source. The motor 448 drives the gear box 452, which drives the motor bevel gear 454, in turn driving the drive bevel gear 456. The drive bevel gear 456 rotates, causing the drive shaft 458 to advance and retract. The drive shaft 458 fully advances distally and then fully retracts proximally the cutting assembly, representing one full cutting stroke.

In the event of a failure, the stationary grip 422 can be moved downward away from the proximal handle portion 410 to cause the device 400 to enter a bailout mode. Downward movement of the stationary grip 422 separates the wires 437 at the connection 436 to communication between the processor and the motor 448, preventing accidental activation of the motor 448 in the bailout mode. The stationary grip 422 remains coupled to the motor 448 and the gear box 452 in the bailout mode, and the motor 448 and the gear box 452 remain engaged with the motor bevel gear 454 due to telescoping of the extendable shaft 434. Upon rotation of the stationary grip 422 in the bailout mode, the motor 448 and the gear box 452 are both rotated with the stationary grip 422. The stationary grip 422 can be manually rotated in the bailout mode to cause the motor 448 and the gear box 452 to rotate the motor bevel gear 454, which can rotate the drive bevel gear 456 and ultimately drive the drive shaft 458 to retract the cutting assembly.

The stationary grip 422 is configured to allow rotation in either direction to allow both advancement and retraction of the cutting assembly. Other variations can allow rotation of the stationary grip in only one direction to allow only retraction of the cutting assembly. The cutting assembly can be retracted as long as the stationary grip is rotated. Other embodiments can include mechanisms to prevent over-retraction, such as a stopper positioned in the path of retraction in the proximal handle portion to contact the cutting assembly and prevent further retraction.

The stationary grip 422 is configured to rotate both the motor 448 and the gear box 452 together. Other embodiments can allow the motor to be rotated with the stationary grip while the motor rotates the gear box (as would occur in the normal mode) so that the motor and the gear box do not rotate together. Such an embodiment can be effective, for example, if the motor is connected to a gear box with a high mechanical advantage ratio.

The surgical device 400 can be reused and returned to the normal mode by depressing the locking arms 430 and moving the stationary grip 422 back to the stationary grip's normal mode position, which will reconnect the motor 448 and the processor. Other variations can prevent the surgical device from being reused, effectively disabling the device, to prevent a malfunctioning surgical device from being used in other operations. For example, the stationary grip can be irreplaceable, such as by adding a tab that would prevent the stationary grip from moving back into the normal mode position and causing communication between the motor and the processor to be permanently disabled or through software upon detection of downward movement of the stationary grip. Alternatively, the locking arms could permanently lock into place once extended.

Figure 8:
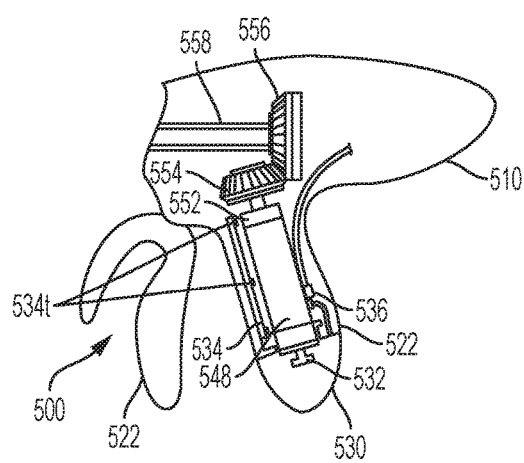
FIG. 8 is a partial side cutaway view of another embodiment of a powered surgical device with a bailout mechanism.
Figure 9:
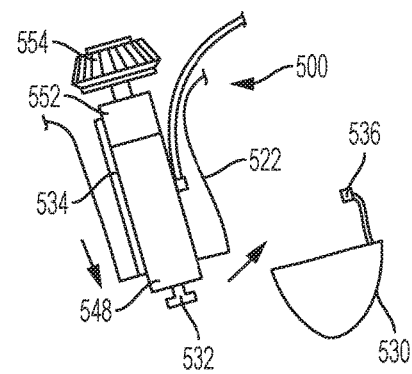
FIG. 9 is a partial side cutaway view of the powered surgical device of FIG. 8.

FIGS. 8-9 illustrate another embodiment of a surgical device 500 having a mechanical bailout. The surgical device 500 can generally be configured and used similar to the surgical devices 100, 200 of FIGS. 1-4. Surgical device 500 has a shaft portion (not shown), and a proximal handle portion 510 including a closure grip 520 and a stationary grip 522. The surgical device 500 has a firing actuator (not shown) that can be configured to advance distally and/or retract proximally a cutting assembly through an end effector (not shown) positioned on a distal end of the shaft portion. The closure grip 520 is effective to move jaws of the end effector between open and closed positions. The firing actuator is connected to and in communication with a processor (not shown) within the proximal handle portion 510. The processor is connected to and in communication with a motor 548 and a power source (not shown) such as a battery. The motor 548 is operably coupled to a gear box 552 and is disposed in the proximal handle portion 510. The motor 548 and the gear box 552 can be operatively coupled to a motor bevel gear 554 that is operably coupled (directly or indirectly) to a drive bevel gear 556, which in turn moves a drive shaft 558 proximally or distally.

In this embodiment, a cap 530 is removably coupled to a bottom of the stationary grip 522. A rotation knob 532 is disposed within the cap 530 and is coupled to the motor 548. A locking arm 534 can extend alongside the motor 548 and the gear box 552 but it can be displaced from the motor 548 and the gear box 552 by a ridge along an edge of the cap 530 by the motor 548, allowing the motor 548 and the gear box 552 to rotate with respect to one another. In other words, the ridge of the cap 530 is located between the motor 548 and the locking arm 534, holding the locking arm 534 a distance away from the motor 548.

The cap 530 is configured to be removable from the stationary grip 522, at which point the rotation knob 532 is exposed and available for rotation. Removal of the cap 530 is configured to lock the motor 548 and the gear box 552 to rotate together, for example by engagement of the locking arm 534. Upon movement of the cap 530 away from the motor 548, the ridge of the cap 530 is pulled away from the locking arm 534 thereby allowing the locking arm 534 to move against the motor 548 and the gear box 552 and to mechanically engage with each of the motor 548 and the gear box 552 through engagement tabs 534t on the locking arm 534. Because the locking arm 534 will mechanically engage with both the motor 548 and the gear box 552, any subsequent rotation of either the motor 548 or the gear box 552 will cause both the motor 548 and the gear box 552 to rotate together. While engagement tabs 534t and the locking arm 534 are illustrated in this embodiment, any mechanism can be used to lock the motor and the gear box together to cause the motor and the gear box to rotate as a single unit, such as bars, cages, internal components between the motor and the gear box, etc. Rotation of the rotation knob 532 is configured to rotate both the motor 548 and the gear box 552 together.

Removal of the cap 530 can also be configured to break communication at a connection 536 between the motor 548 and the processor. The cap 530 can mechanically end communication between the processor and the motor 548 by physically breaking a connection between the motor 548 and the processor that is maintained by wires running through the cap 530. Upon removal of the cap, the wires can separate from one another, ending communication between the processor and the motor 548, as seen in FIG. 9. Ending communication between the processor and the motor can be accomplished in a variety of different ways known in the art. For example, a sensor in the cap can detect removal of the cap and can send a signal to the processor that the bailout mode has been entered, at which point the processor can stop all signals to the motor until the normal mode is resumed. In such an embodiment, a connection between the motor and the processor would not run through the cap.

When the device 500 is in a normal mode, the cap 530 remains in place and communication between the processor and the motor 548 is maintained. Actuation of the firing actuator sends a signal to the processor. The processor provides power to the motor 548 from the power source. The motor 548 drives the gear box 552, which drives the motor bevel gear 554, in turn driving the drive bevel gear 556. The drive bevel gear 556 rotates, causing the drive shaft 558 to advance and retract. The drive shaft 558 fully advances distally and then fully retracts proximally the cutting assembly, representing one full cutting stroke.

Upon removal of the cap 530, the device 500 enters a bailout mode. Removal of the cap 530 ends communication between the processor and the motor 548, preventing accidental activation of the motor 548 in the bailout mode. As seen in FIG. 9, the cap 530 in the bailout mode is separated from the device 500, exposing the rotation knob 532. However, the cap 530 can optionally be hingedly or otherwise coupled to the stationary grip 522 in a manner that provides access to the rotation knob 532. The rotation knob 532 is rotated to rotate the motor 548 and the gear box 552 in the bailout mode, both of which remain in engagement with the motor bevel gear 554. Upon rotation of the rotation knob 532, the motor 548 and the gear box 552 rotate together to drive the motor bevel gear 554, which can drive the drive bevel gear 556 and drive the drive shaft 558 to retract the cutting assembly.

The rotation knob 532 is configured to allow rotation in either direction to allow both advancement and retraction of the cutting assembly. Other variations can allow rotation of the rotation knob in only one direction to allow only retraction of the cutting assembly, for example by using a single-direction ratchet. The cutting assembly can be retracted as long as the rotation knob is rotated. Other embodiments can include mechanisms to prevent over-retraction, such as a stopper positioned in the path of retraction in the proximal handle portion to contact the cutting assembly and prevent further retraction.

The cap 530 is configured to lock the motor 548 and the gear box 552 together during the bailout mode through engagement of the locking arm 534 such that the motor 548 and the gear box 552 rotate together. Other embodiments can allow the motor to be rotated with the rotation knob while the motor rotates the gear box (as would occur in the normal mode) so that the motor and the gear box do not rotate together. Such an embodiment can be effective, for example, if the motor is connected to a gear box with a high mechanical advantage ratio.

The surgical device 500 can be reused and returned to the normal mode by replacing the cap 530, which will reconnect the motor 548 and the processor and unlock the motor 548 and the gear box 552 from one another to allow individual rotation. Other variations can prevent the surgical device from being reused, effectively disabling the device, to prevent a malfunctioning surgical device from being used in other operations. For example, the cap can be irreplaceable, such as by adding a tab that would interfere with the cap to prevent the cap from being reattached to the stationary grip and causing communication between the motor and the processor to be permanently disabled or through software upon detection of removal of the cap.

Figure 10:
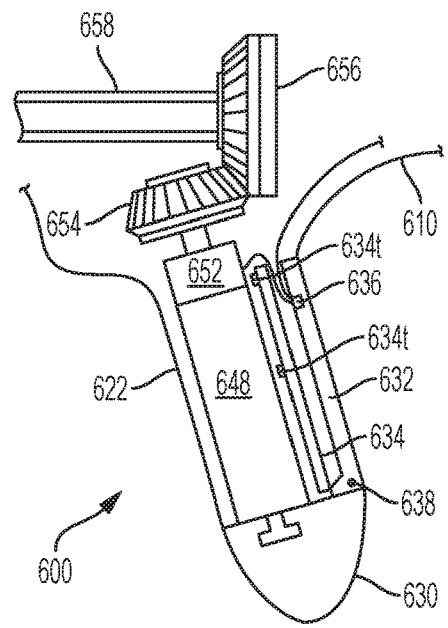
FIG. 10 is a partial side cutaway view of another embodiment of a powered surgical device with a bailout mechanism.
Figure 11:
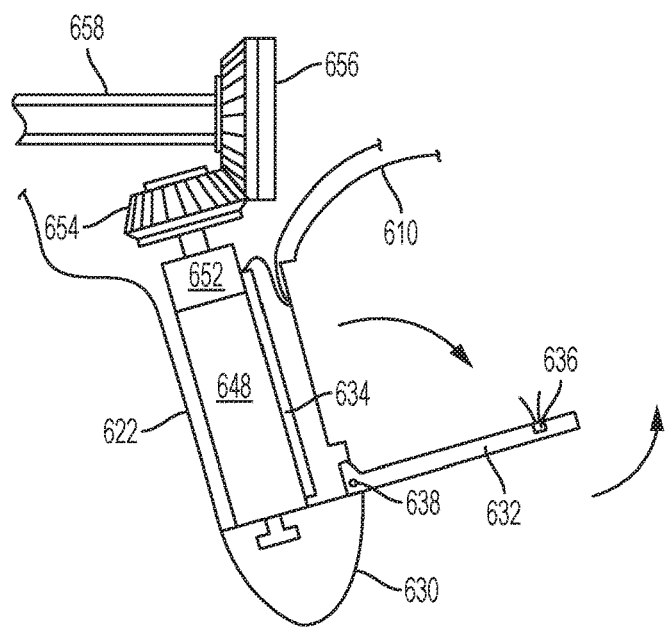
FIG. 11 is a partial side cutaway view of the powered surgical device of FIG. 10.

FIGS. 10-11 illustrate another embodiment of a surgical device 600 having a mechanical bailout. The surgical device 600 can generally be configured and used similar to the surgical devices 100, 200 of FIGS. 1-4. Surgical device 600 has a shaft portion (not shown), and a proximal handle portion 610 including a closure grip (not shown) and a stationary grip 622. The surgical device 600 has a firing actuator (not shown) that can be configured to advance distally and/or retract proximally a cutting assembly through an end effector (not shown) positioned on a distal end of the shaft portion. The closure grip 620 is effective to move jaws of the end effector between open and closed positions. The firing actuator is connected to and in communication with a processor (not shown) within the proximal handle portion 610. The processor is connected to and in communication with a motor 648 and a power source (not shown) such as a battery. The motor 648 is operably coupled to a gear box 652 and is disposed in the proximal handle portion 610. The motor 648 and the gear box 652 can be operatively coupled to a motor bevel gear 654 that is operably coupled (directly or indirectly) to a drive bevel gear 656, which in turn moves a drive shaft 658 proximally or distally.

In this embodiment, a cap 630 is coupled to a bottom of the stationary grip 622 and is also coupled to an end of the motor 648 opposite to the gear box 652. A lever 632 is coupled to the cap 630 at a pivot point 638. The lever 632 is movable about the pivot point 638 from a first position coupled to the stationary grip 622 to a second position away from the stationary grip 622 and perpendicular to the stationary grip 622. The cap 630 is not rotatable in relation to the stationary grip 622 when the lever 632 is in the first position in place against the stationary grip 622. In the first position, the lever 632 rests in a cavity or recess in an upper portion of the stationary grip 622 so the cap 630 is prevented from rotating. A locking arm 634 can extend alongside the motor 648 and the gear box 652 but be displaced from the motor 648 and the gear box 652 by a bulbous portion at an end of the lever 632 by the pivot point 638, allowing the motor 648 and the gear box 652 to rotate with respect to one another. In other words, the bulbous point of the lever 632 supports the locking arm 634 to maintain the locking arm 634 at a location out of engagement with the motor 648 and holding the locking arm 534 a distance away from the motor 648.

The cap 630 is rotatable in relation to the stationary grip 622 when the lever is moved to the second position away from the stationary grip 622. In the second position, the lever 632 is detached from the upper portion of the stationary grip 622, so movement of the lever 632 causes rotation of the cap 630. Movement of the lever 632 is configured to lock the motor 648 and the gear box 652 to rotate together, for example by engagement of the locking arm 634. Upon movement of the lever 632 away from the motor 648, the bulbous portion of the lever 632 will rotate about pivot point 638 and a curved surface of the bulbous point of the lever 632 will push the locking arm 634 to move against the motor 648 and the gear box 652 and to mechanically engage with each of the motor 648 and the gear box 652 through engagement tabs 634t on the locking arm 634. Because the locking arm 634 will mechanically engage with both the motor 648 and the gear box 652, the motor 648 and the gear box 652 will be rotationally mated to one another. While engagement tabs 634t and the locking arm 634 are illustrated in this embodiment, any mechanism can be used to lock the motor and the gear box together to cause the motor and the gear box to rotate as a single unit, such as bars, cages, internal components between the motor and the gear box, etc. The cap 630 is coupled to and not rotatable in relation to the motor 648. Movement of the lever 632 to the lever's second position and rotation of the lever 632 and the cap 630 in relation to the stationary grip 622 is configured to rotate both the motor 648 and the gear box 652 together. Movement of the lever 632 is configured to break communication at a connection 636 between the motor 648 and the processor.

The lever 632 mechanically ends communication between the processor and the motor 648 by physically breaking a connection between the motor 648 and the processor formed by wires that also run through the lever 632. Upon moving the lever 632 to the second position, the wires are physically separated at connection 636, as seen in FIG. 11. Ending communication between the processor and the motor can be accomplished in a variety of different ways known in the art. For example, a sensor in the lever can detect moving the lever from its first position into its second position and can send a signal to the processor that the bailout mode has been entered, at which point the processor can stop all signals to the motor until the normal mode is resumed. In such an embodiment, wires for the connection between the motor and the processor would not run through the lever.

When the device 600 is in a normal mode, the cap 630 and the lever 632 remain in place and communication between the processor and the motor 648 is maintained. Actuation of the firing actuator sends a signal to the processor. The processor provides power to the motor 648 from the power source. The motor 648 drives the gear box 652, which drives the motor bevel gear 654, in turn driving the drive bevel gear 656. The drive bevel gear 656 rotates, causing the drive shaft 658 to advance and retract. The drive shaft 658 fully advances distally and then fully retracts proximally the cutting assembly, representing one full cutting stroke.

In the event of a failure, the lever 632 can be moved away from the stationary grip 622 to cause the device 600 to enter a bailout mode. As seen in FIG. 11, the lever 632 in the bailout mode is rotated to rotate the cap 630, which in turn rotates the motor 648 and the gear box 652. The motor 648 and the gear box 652 do not move out of engagement with the motor bevel gear 654, so upon rotation of the lever 632 and the cap 630, the motor 648 and the gear box 652 rotate together to drive the motor bevel gear 654, which can drive the drive bevel gear 656 and ultimately drive the drive shaft 658 to retract the cutting assembly.

The lever 632 and the cap 630 are configured to allow rotation in either direction to allow both advancement and retraction of the cutting assembly. Other variations can allow rotation of the lever and the cap in only one direction to allow only retraction of the cutting assembly, for example by using a single-direction ratchet. The cutting assembly can be retracted as long as the lever and the cap are rotated. Other embodiments can include mechanisms to prevent over-retraction, such as a stopper positioned in the path of retraction in the proximal handle portion to contact the cutting assembly and prevent further retraction.

The lever 632 is configured to lock the motor 648 and the gear box 652 together during the bailout mode through engagement of the locking arm 634 such that the motor 648 and the gear box 652 rotate together. Other embodiments can allow the motor to be rotated with the lever and the cap while the motor rotates the gear box (as would occur in the normal mode) so that the motor and the gear box do not rotate together. Such an embodiment can be effective, for example, if the motor is connected to a gear box with a high mechanical advantage ratio.

The surgical device 600 can be reused and returned to the normal mode by returning the lever 632 to its first position coupled to the stationary grip 622, which will reconnect the motor 648 and the processor and unlock the motor 648 and the gear box 652 from one another to allow individual rotation. Other variations can prevent the surgical device from being reused, effectively disabling the device, to prevent a malfunctioning surgical device from being used in other operations. For example, the lever can be irreplaceable, such as by adding a tab that would interfere with the lever to prevent the lever from being reattached to the stationary grip and causing communication between the motor and the processor to be permanently disabled or through software upon detection of movement of the lever.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device," incorporated herein by reference in its entirety. It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a handle portion having an elongate shaft extending distally therefrom, the elongate shaft having first and second jaws at a distal end thereof, the jaws being configured to engage tissue therebetween;
   a cutting assembly configured to move relative to the first and second jaws so as to cut tissue engaged between the first and second jaws;
   a drive shaft extending from the handle through the elongate shaft and being coupled to the cutting assembly for moving the cutting assembly relative to the first and second jaws;
   a gear box coupled to the drive shaft for moving the drive shaft proximally and distally; and
   a motor coupled to the gear box for driving the gear box;
   wherein the device has a normal mode in which power can be provided to the motor to drive the gear box and thereby cause movement of the drive shaft, and the device has a bailout mode in which the motor and gear box can be manually rotated as a unit to cause movement of the drive shaft, and power is disconnected from the motor in the bailout mode.

2. The device of claim 1, wherein the handle portion includes a shroud around the motor and gear box that is configured to separate from the handle portion in the bailout mode.

3. The device of claim 2, wherein the shroud is configured to reconnect to the handle portion to transition back to the normal mode.

4. The device of claim 1, wherein a cap on the end of the handle portion is movable from a first position in which the cap is mated to the handle portion to a second position in which the cap is partially separated from the handle portion and is freely rotatable relative to the handle portion, rotation of the cap causing rotation of the motor and the gear box.

5. The device of claim 4, wherein power is disconnected from the motor when the cap is moved to the second position.

6. The device of claim 1, wherein a lever on the end of the handle portion is movable from a first position in which the lever is coupled to a part of the handle portion to prevent rotation of the motor and the gear box to a second position in which the lever is moved away from the part of the handle portion, the lever being rotatable relative to the handle portion when in the second position, rotation of the lever causing rotation of the motor and the gear box.

7. The device of claim 6, wherein movement of the lever to the second position causes power to be disconnected from the motor.

8. The device of claim 1, wherein a cap on the end of the handle portion is removable from the handle portion, and a knob is coupled to an end of the motor and is accessible upon removal of the cap, the knob being configured to cause rotation of the motor and the gear box upon rotation of the knob.

9. A surgical device, comprising:
   a handle having an elongate shaft extending distally therefrom, the elongate shaft having first and second jaws at a distal end thereof for engaging tissue therebetween;
   a cutting assembly movable relative to the first and second jaws so as to cut tissue engaged between the first and second jaws;
   a motorized gear assembly coupled to the cutting assembly for moving the cutting assembly relative to the first and second jaws; and
   a bailout lever positioned on the handle and movable from a first disengaged position, in which the bailout lever is disengaged with the motorized gear assembly, to a second engaged position, in which the bailout lever is engaged with the motorized gear assembly and is effective to manually drive the motorized gear assembly, and movement of the bailout lever to the second engaged position causes power to be disconnected from the motorized gear assembly.

10. The surgical device of claim 9, wherein movement of the bailout lever from the second engaged position back to the first disengaged position causes power to be reconnected to the motorized gear assembly.

11. The surgical device of claim 9, wherein movement of the bailout lever to the second engaged position causes the bailout lever to be positioned partially off of the handle.

12. The surgical device of claim 9, wherein the bailout lever is configured to rotate the motorized gear assembly in the second engaged position.

* * * * *